United States Patent [19]
Brothers et al.

[11] Patent Number: 5,478,315
[45] Date of Patent: Dec. 26, 1995

[54] LOCAL ANESTHETIC INJECTION SYSTEM

[75] Inventors: William S. Brothers; Brian H. Brothers, both of Provo, Utah

[73] Assignee: Brothers Family Investments, L.C., Provo, Utah

[21] Appl. No.: 291,931

[22] Filed: Aug. 8, 1994

[51] Int. Cl.⁶ .................................................. A61M 5/00
[52] U.S. Cl. ............... 604/115; 604/117; 604/187
[58] Field of Search ........................ 604/115, 187, 604/212, 197, 117, 174

[56] References Cited

U.S. PATENT DOCUMENTS

| | | |
|---|---|---|
| Re. 25,637 | 9/1964 | Kravitz et al. . |
| D. 198,658 | 7/1954 | Smeton . |
| 1,934,046 | 11/1933 | Demarchi . |
| 2,457,464 | 12/1948 | Grose . |
| 2,855,932 | 10/1958 | Stubbs . |
| 2,944,549 | 7/1960 | Alexander ........................ 604/212 X |
| 2,945,496 | 7/1960 | Fosdal . |
| 3,466,131 | 9/1969 | Arcudi . |
| 3,826,259 | 7/1974 | Bailey . |
| 3,920,001 | 11/1975 | Edwards . |
| 4,072,249 | 2/1978 | Ekenstam et al. ............... 604/212 X |
| 4,299,219 | 11/1981 | Norris, Jr. . |
| 4,373,526 | 2/1983 | Kling ................................. 604/117 |
| 4,662,376 | 5/1987 | Belanger . |
| 4,878,897 | 11/1989 | Katzin ................................. 604/86 |
| 5,087,262 | 2/1992 | Sheahon . |
| 5,122,056 | 6/1992 | Barbee . |
| 5,141,496 | 8/1992 | Dalto et al. ........................ 604/117 |
| 5,190,521 | 3/1993 | Hubbard et al. . |
| 5,199,952 | 4/1993 | Marshall, Sr. et al. ............ 604/156 |
| 5,224,940 | 7/1993 | Dann et al. . |
| 5,267,974 | 12/1993 | Lambert ............................. 604/195 |
| 5,273,528 | 12/1993 | Skeen et al. . |
| 5,320,607 | 6/1994 | Ishibashi ............................. 604/115 |

*Primary Examiner*—John G. Weiss
*Attorney, Agent, or Firm*—M. Reid Russell

[57] ABSTRACT

A local anesthetic injection system that is suitable for use with smaller children for providing an essentially pain free injection of a local anesthesia into a child's epidermis skin layer, above nerve endings, to deaden that skin area to receive an injection of a medicine through that deadened area utilizing a conventional hypodermic needle. The several embodiments of the system include a body that has a cup arrangement with a flat edge upstanding wall and is open thereacross. The cup is arranged to receive a force applied to the top thereof to urge the cup flat edge into the surface of a section of skin whereon the cup rests, causing the skin within the cup to be formed into a dome shape. A small hollow needle is maintained within the cup such that an open bevel needle end extends at an angle just below the plane of the cup edge. Thereby, as the dome of skin is formed within the cup the needle bevel end tends to travel into the dome of skin, above the skin nerve endings, allowing a vessel connecting to the needle to dispense a local anesthesia through the hollow needle bevel end when an operator applies a pressure generating force thereto.

3 Claims, 4 Drawing Sheets

LOCAL ANESTHETIC INJECTION SYSTEM

BACKGROUND OF THE INVENTION

1. Field of the Invention

The present invention concerns the field of apparatus and procedures for delivery of a liquid anesthetic into a patient's epidermis skin layer to deaden the skin at that point of injection to receive a shot utilizing a conventional hypodermic needle.

2. Prior Art

A number of devices are presently available for injecting or topically applying a variety of chemicals into or onto a patient's skin for deadening that area to a subsequent medical procedure. None, however, have involved, as does the present invention, a device for guiding a small needle nearly horizontally into the skin epidermis layer, and above nerve endings. A liquid anesthetic is administered through the small needle to deaden the skin area so as to provide for a pain free injection at that location utilizing a conventional hypodermic needle.

Examples of devices and systems for their use to provide for deadening an area of a patient's body are shown, for example, in a U.S. Pat. No. 5,122,056, that shows an example of a device for topically applying a lidocaine type chemical onto an area of a dental patient's gums, which, of course, does not involve a use of a needle or the like. A needle arrangement is, however, shown in U. S. Pat. No. 3,920,001, that includes a disk for positioning onto and to be urged against a patient's skin surface, and further includes a guide sleeve connected to the disk at an angle such that a needle passed through the guide sleeve will extend into the patient's skin at an angle to the skin surface. While this arrangement tends to minimize pain, the needle nevertheless passed into the skin to a depth to encounter and stimulate nerves, causing pain to the patient. Distinct therefrom the device of the invention passes a bevel end of a small needle nearly horizontally into the patient's epidermis skin layer to inject a liquid anesthetic therein without contacting a nerve or nerves, as could cause the patient pain.

Functionally and structurally unlike the present invention a number of devices are available that provide for elevating a section of a patient's skin to pass a needle therein, as shown, for example, in U. S. Pat. Nos. 5,273,528; Re 25,637; 5,190,521; 3,826,259 and 3,466,131. Further, and also functionally and structurally unlike the present invention a number of devices are available for elevating a section of a patient's skin utilizing a vacuum, and some such devices are shown, for example, in U.S. Pat. Nos. 4,299,219; 2,945, 496; and 1,934,046. Additionally, a device for depressing sections of skin to elevate an area therebetween for receiving a needle is shown in U.S. Pat. No. 2,457,464. This arrangement, however, does not show the cup structure of the invention nor the needle arrangement thereof whereby a small hypodermic needle is passed, close to the horizontal, into a patient's epidermis so as not to contact any nerve endings.

BRIEF SUMMARY OF THE INVENTION

It is therefor a principal object of the present invention in a local anesthetic injection system to provide a device for injecting an anesthetic chemical into a patient's epidermis, just below their skin surface and above nerve endings, for deadening that area to receive a conventional hypodermic needle passed therethrough.

Another object of the present invention is to provide a device for injecting a local anesthetic into a patient's epidermis skin layer that will pass deeper into skin to the nerve endings to deaden that area to pain to receive a shot with a conventional hypodermic needle passed therethrough.

Another object of the present invention is to provide a device that is particularly well suited for use with young children to deaden an area of their skin to receive a pain free injection utilizing a conventional hypodermic needle.

Still another object of the present invention is to provide embodiments of the invention that have an attractive and/or toy like appearance to children that are both easy and effective to use to pass a bevel end of a small hypodermic needle at an angle close to the horizontal into a patient's epidermis skin layer, above their nerve endings, so as to deaden that skin area to receive an essentially pain free injection utilizing a conventional hypodermic needle.

In accordance with the above objects, the present invention is in a local anesthetic injection system for delivery of an anesthetic agent, such as lidocaine, into an epidermis layer of a patient's skin, and above their nerve endings at that location. The injection to provide a local deadening effect thereto to allow for the administration of essentially a pain free injection through that deadened area utilizing a conventional hypodermic needle. Different embodiments of the invention each include an arrangement for lifting a section of a patient's skin and for passing an end of a small hypodermic needle therein.

In practice, so as to pass the small needle at an angle close to the horizontal, the needle bevel is parallel to the skin surface and travels into a raised skin area. The needle end passes into the epidermis skin layer, through the epidermis stratum corneum, that is the horny top layer of the epidermis. This area is above nerve endings and therefore the needle entry is essentially painless. After entry, an anesthetic, such as lidocaine, is injected, under pressure, out of the small needle bevel end, into the porous tissue below the skin stratum corneum, and flows into the tissues of the dermis, deadening the nerve ends. Whereafter, a painless injection can be administered through the deadened skin area, as with a conventional hypodermic needle.

The system of the invention provides, as a first embodiment, an arrangement of a plunger mounting a long small needle on a discharge end that is fitted through a sleeve. The needle end extends from the sleeve forward end, into the side of a flat cup, and is at an angle of from zero (0) to forty-five (45) degrees from a plane across the cup. The needle is arranged to just extend into the cup interior that includes a flat plate across its top end as the cup base, and is open across its bottom end. So arranged, an operator, utilizing one hand, positions the cup edge onto the surface of an area of skin to be deadened. The cup edge is pressed into that skin surface causing the skin to form a dome within the cup. As the skin surface lifts into a dome, with a small amount of cup into the dome as may be needed the needle pointed bevel end just enters the epidermis skin layer, passing through the stratum corneum. Thereafter, the plunger is depressed and a flow of a local anesthetic, such as lidocaine, is injected through the small needle open bevel end. That anesthetic flows into the skin area within the cup edge to penetrate the skin to the nerve endings therebelow. Thereby, the patient's skin is deadened within and below the cup as a skin area to receive an injection of a medicine from a conventional hypodermic needle, providing an essentially painless injection.

The system of the invention is particularly suited for use with small children for providing an essentially painless injection of a prescribed medicine. As the system is so preferred for use, it is desirable to provide a number of embodiments of the invention that have a pleasing appearance to such child so as not to arouse their fear of pain when they are to receive a local anesthetic to deaden a particular skin surface area. Accordingly, the device of the invention can be arranged in housings having different attractive appearances, but will function essentially as described above to provide for a local deadening of a skin area to receive a shot of a prescribed medication using a conventional hypodermic needle.

THE DRAWINGS

The following drawings illustrate that which is presently regarded as the best modes for carrying out the invention:

FIG. 1 is a profile perspective view of a first embodiment of a local anesthetic injection system of the invention shown as a plunger operated hypodermic whose needle, shown in broken lines, is contained in a sleeve that mounts a flat cylindrical cup on the sleeve forward or distal end, the plunger held in one of an operator's hands and the thumb of the other operator's hand shown engaging the cup top and pushing the edges of the cup side into a patient's skin;

Figure 1:
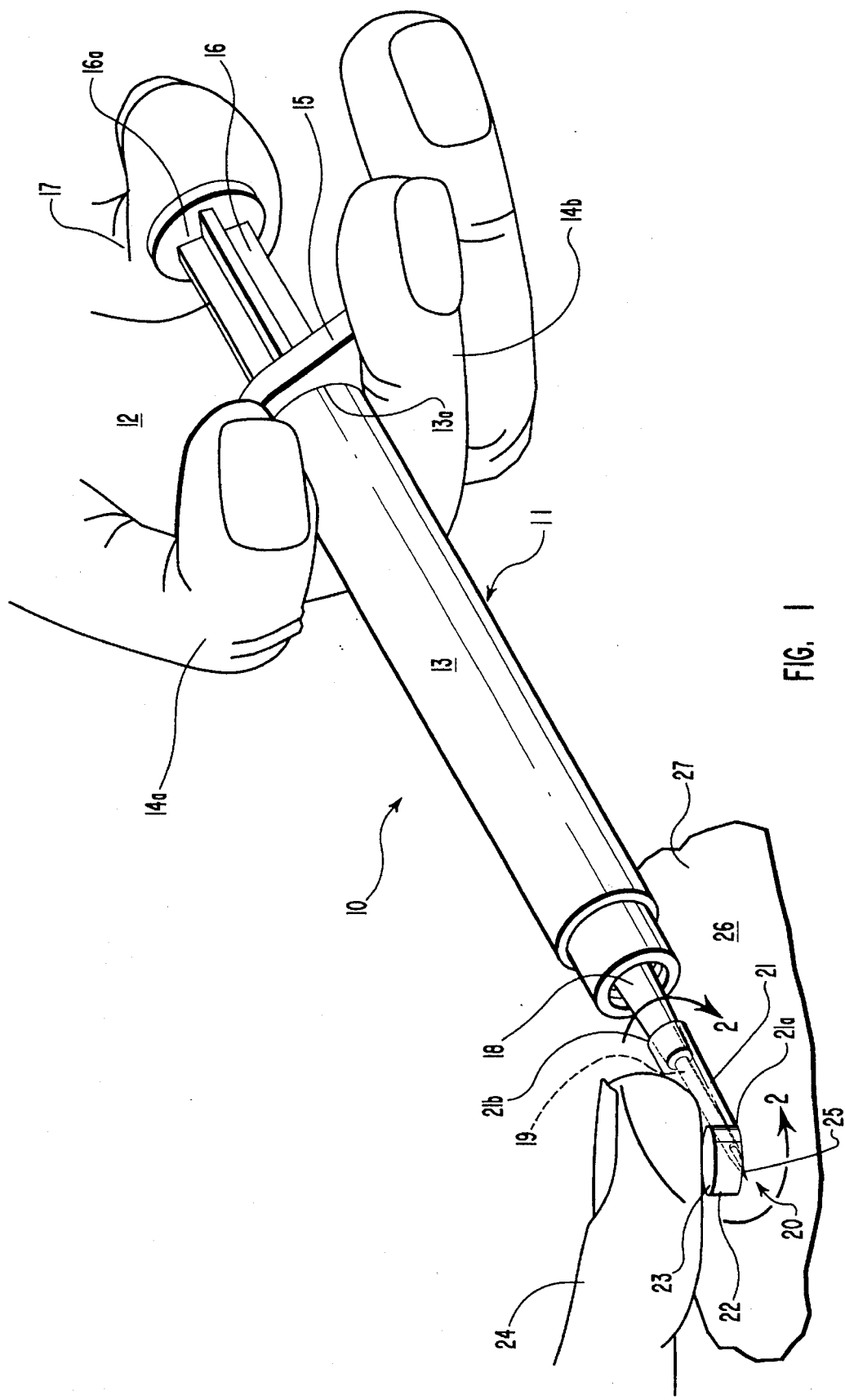
Figure 3:
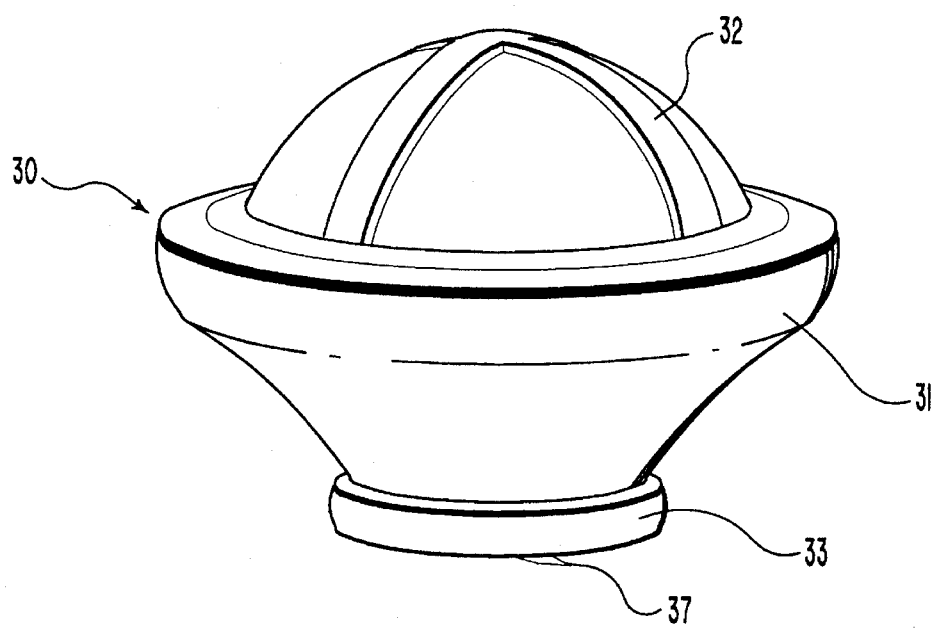
FIG. 3 is a side elevation view of a second embodiment of a local anesthetic injection system of the invention shown positioned on a patient's skin surface.
Figure 4:
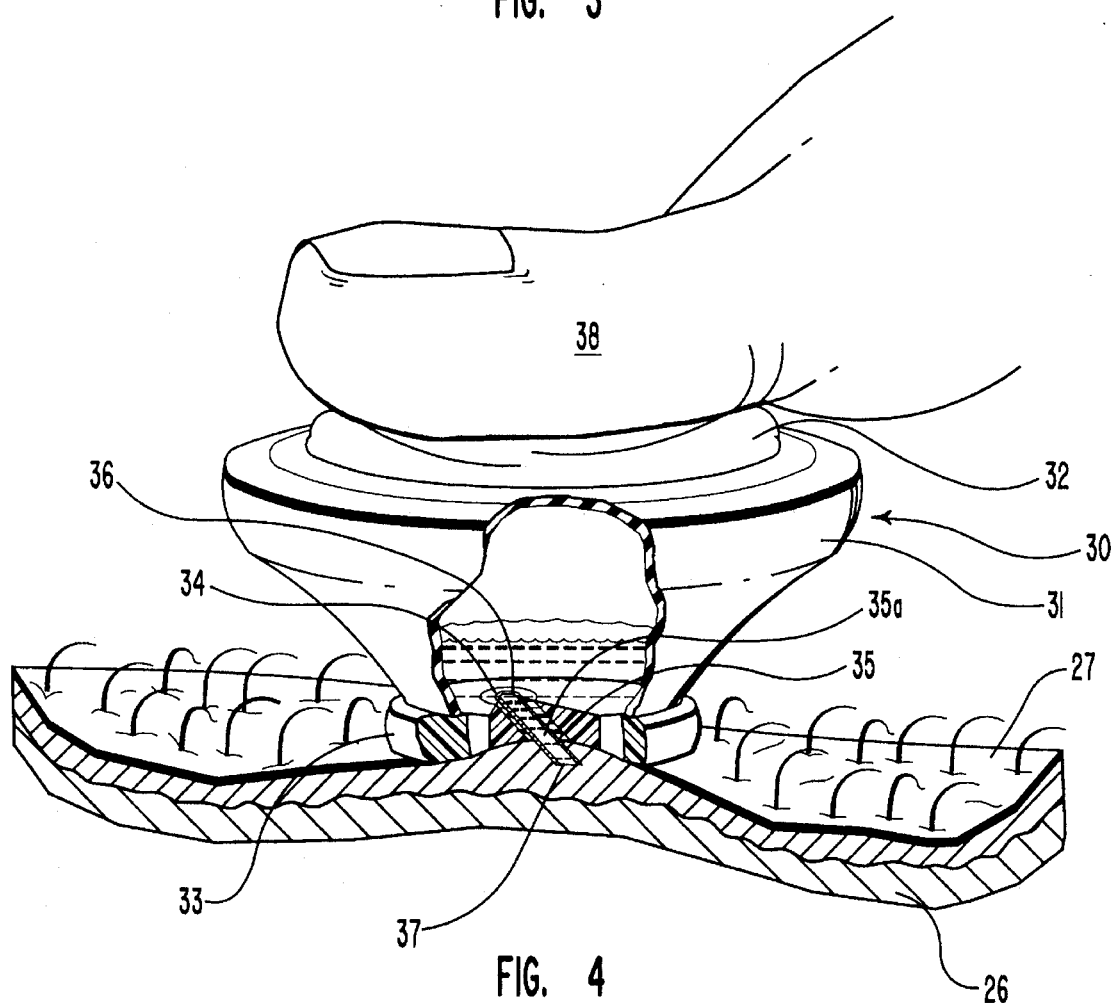
Figure 5:
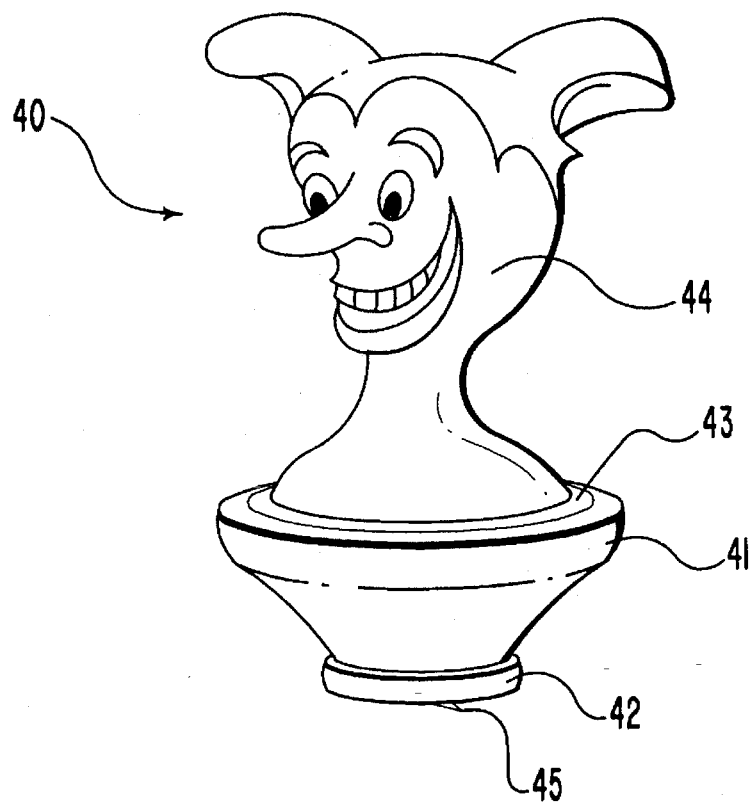
Figure 6:
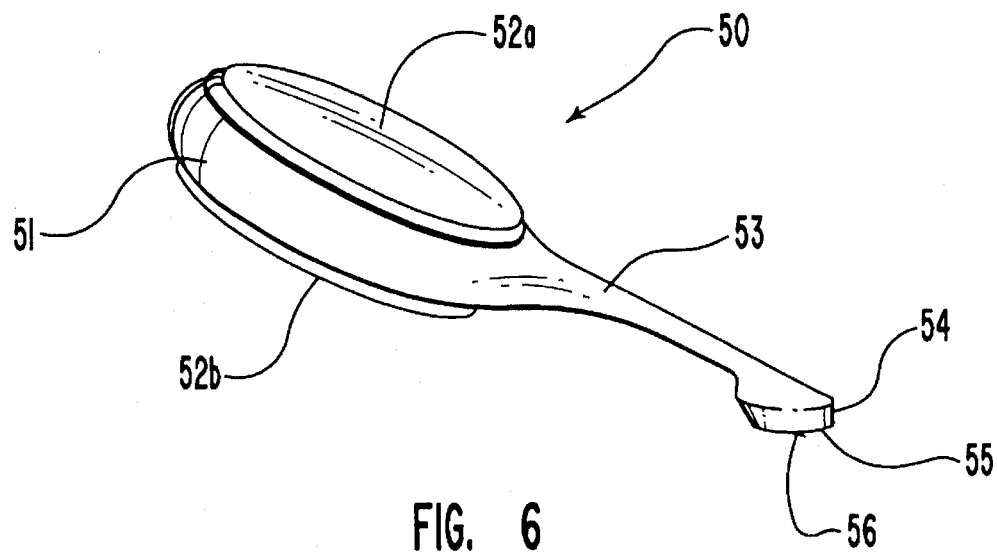

FIG. 4 is an enlarged side elevation view of the embodiment of FIG. 3, showing a housing with a section removed from the side thereof exposing the side of a flexible bulb that is arranged across the housing top and having a discharge neck end connect to a tube end that mounts a small needle on the tube forward or distal end, the needle having an open bevel end shown passed into the patient's skin, and showing an operator's thumb or finger depressing the bulb;

FIG. 5 is a side elevation view of a third embodiment of a local anesthetic injection system of the invention that is like the embodiment of FIG. 3, except the flexible bulb thereof has been replaced with a flexible clown head; and FIG. 6 is a side elevation view of a fourth embodiment of a local anesthetic injection system of the invention that is similar to the embodiment of FIG. 1, except it includes a bellows arrangement replacing the hypodermic to pressurize a flow of a liquid chemical passed through a tube that connects to a small needle.

DETAILED DESCRIPTION

The present invention is in a local anesthetic injection system, hereinafter referred to as system, and a first embodiment of a system 10 is shown in FIG. 1. FIG. 1 shows the system 10 as including a hypodermic syringe 11 held in an operator's hand 12. The hand 12 is shown with a hypodermic cylinder 13 fitted between the operator's index and middle fingers 14a and 14b, respectively, that contact and maintain the cylinder at an outstanding flange 15 extending from around a cylinder head end 13a. A hypodermic plunger 16 extends axially from the cylinder head end 13a that has a flat disk 16a formed across its top end. Which flat disk 16a is shown engaged by a thumb 17 of the operator's hand 12. Depression of the plunger 16 into cylinder 13 urges a fluid contained therein out of a hypodermic nozzle end 18 to pass through a needle 19, shown in broken lines, and out a needle bevel 25 end.

Figure 2:
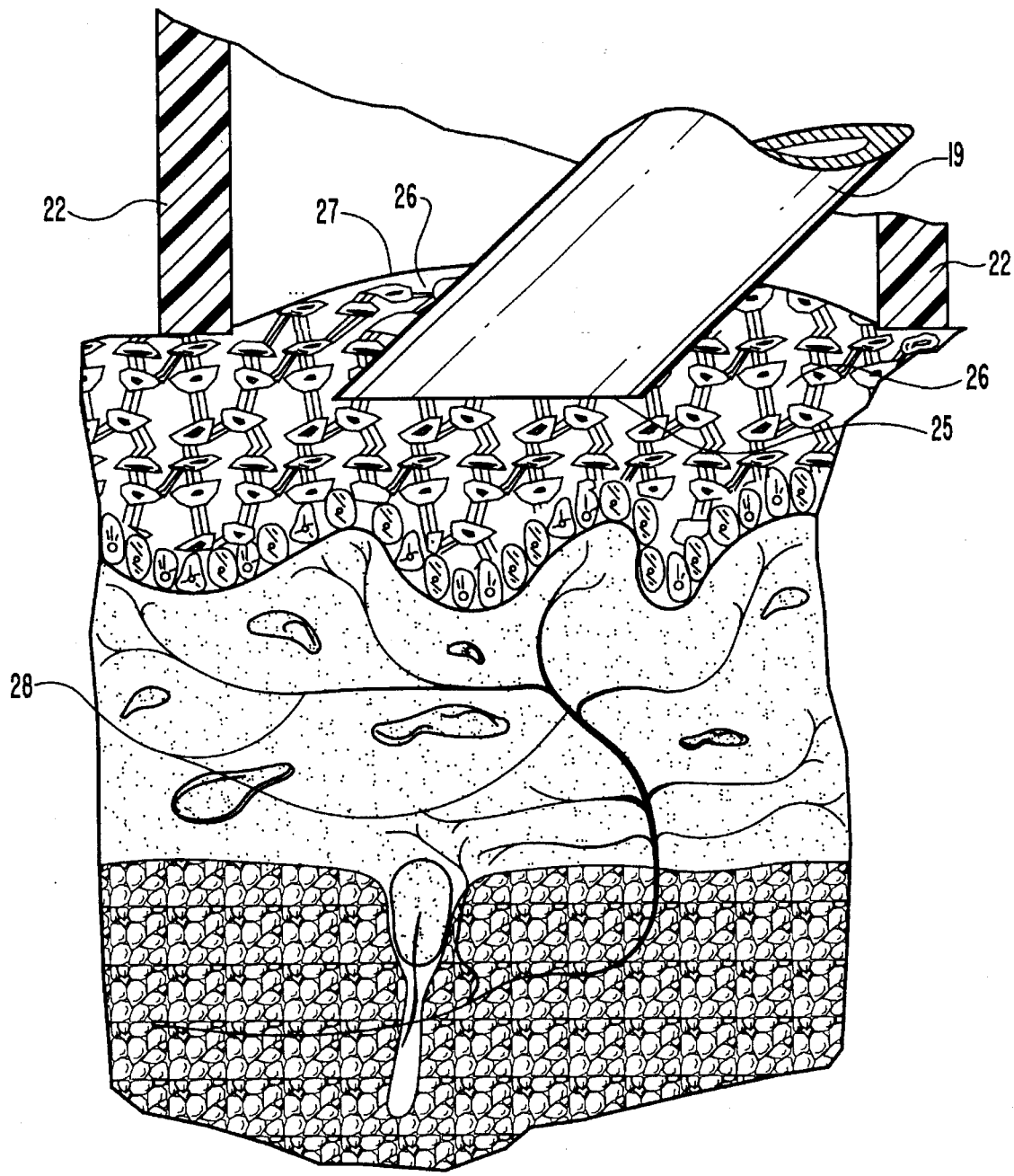
FIG. 2 is an enlarged sectional view taken within the line 2—2 of FIG. 1 showing the cup edge urged into the top layer of the patient's skin, causing the skin to bulge outwardly into a dome shape, the needle end that extends slightly below the cup edge, is shown as having passed through the epidermis stratum corneum layer, and showing the needle bevel as essentially parallel to the skin surface.

The hypodermic syringe 11 is preferably a standard readily available syringe fitted with needle 19 that, it should be understood, is a small needle. Preferably a thirty (30) gauge needle that is 0.5 mm in diameter, that includes a flat bevel 25 and is approximately one (1) mm in length is utilized as needle 19. In practice, as shown in FIG. 2, the needle bevel 25 end is passed into the skin 26 epidermis, passing just below the skin surface 27, with the bevel 25 to be approximately parallel to that skin 26 top surface 27, or stratum corneum. To control needle bevel end positioning the invention includes an inverted cup 20 that is linked by a sleeve 21 to the hypodermic syringe nozzle end 18 and wherein the needle 19 extends. In which arrangement, the needle bevel 25 end just extends into the cup interior, as shown in FIG. 1. The sleeve 21 is open longitudinally therethrough and is secured on a forward or distal end 21a into a side wall 22 of cup 20, and has its opposite rear or proximal end 21b fitted over to provide a friction fit to the hypodermic nozzle end 18. The sleeve 21 distal end 21a is slid to a point along the hypodermic nozzle end 18 to where the needle 19 bevel 25 end extends into the cup 20 interior and just below the end of side wall 22.

In practice, a cup top surface 23 is engaged by the operators thumb 24 that pushes downwardly thereon, to urge the cup wall 22 edge into the patient's skin 26, as shown best in FIG. 2. The cup wall edge when urged into the skin 26 causes the area of skin within the cup interior to flow upwardly and form a dome shape. During which skin flow, and with a slight applied pressure on the cup top surface 23 to urge it into the dome, as may be needed, the needle bevel 25 end travels into the skin epidermis layer to a point just below the skin top surface 27, or stratum corneum. The needle bevel 25 end thereby passes into the epidermis layer, at an angle of from zero (0) to forty-five (45) degrees to the skin surface selected to maintain the needle bevel 25 at essentially a parallel attitude to the skin top surface 27.

The needle bevel 25 end, as shown, is inserted into the epidermis, above nerve endings 28. Accordingly, in the installation of the needle bevel 25 end the nerve endings are not contacted as could cause the patient pain. The skin epidermis 26 below the top surface of the stratum corneum 27 is porous to allow fluids to flow therethrough. Accordingly, with the needle bevel 25 end installed in the skin 26, as shown in FIG. 2, the operator can urge the plunger 16 slowly into the cylinder 13, injecting the anesthetizing fluid into the skin epidermis that then flows to the nerve ending 28, anesthetizing them. During which injection, the needle 19 should remain immobile to avoid further needle penetration as could contact the nerve endings 28. The needle 19 can then be removed and, after a passage of sufficient time to allow for the nerve endings to be deadened, an injection of a medication can be administered through the deadened area using a conventional hypodermic needle without the patient suffering pain.

FIG. 3 shows a second embodiment 30 of a local anesthetic injection system of the invention that, like the system 10, is for injection of a local anesthetic, such as lidocaine, into a patient's epidermis 26 skin layer, just below the epidermis stratum corneum 27, and above nerve endings 28, as shown in FIG. 2. Which injection is to deaden that skin area to receive an injection of a medication utilizing a conventional hypodermic needle.

Distinct from system 10, the system 30 is designed for operation utilizing a single operator's hand and provides an attractive appearance that has an aesthetically calming effect on a patient who is a young child. Shown in FIGS. 3 and 4, the system 30 is formed to have the appearance of a child's toy top, having a body with a broad round mid-section 31 that slopes inwardly therefrom to a rounded or dome shaped top 32, and is sloped inwardly into a round bottom neck 33. Preferably, the rounded top 32 is half of a bulb that contains the liquid medication shown in FIG. 4 as waves, with the other half maintained in the body, and is formed from a flexible material, such as rubber or plastic. The dome shaped top 32, when depressed as shown in FIG. 4, pressurizes air above the liquid urging that liquid to flow from a nozzle end 34. Which nozzle end 34 is shown through a removed section as a flat section of material formed across to close across the bulb lower end. The flat section of material forming nozzle end 34, as shown, mounts an end of a tube 35 that contains, axially mounted therein, a needle 36. An end of needle 36, that includes an open bevel 37, as shown in FIGS. 3 and 4, and is arranged to project just below the system bottom neck 33. The needle bevel 37 end is preferably angled to a plane across that bottom neck that is the same angle to the horizontal as the needle 19 bevel end 25 of system 10 of FIGS. 1 and 2 forms to a plane across the cup side wall 22 lower edge.

As set out above, the system 30 is operated by an operator who positions the bottom neck 33 thereof, as shown in FIG. 4, onto the surface 27 of skin 26, and depresses the top of rounded top 32 with their thumb 38. The bulb is thereby compressed to pressurize a column of fluid 35a in a lower portion there that is urged through the tube 35 and out through the connected needle 36. By depressing the rounded top 32, as shown, the lower edge of bottom neck 33 is urged into skin 26, forming a dome within the neck that is like that shown in FIG. 2. The skin surface 27 of that dome, as it is formed, and with travel of the bottom neck 33 into the dome as may be needed, the bevel 37 end of needle 36 will pass under that top layer 27, that is the stratum corneum, and into the epidermis therebelow, above the nerve endings. As the nerve endings are not contacted a patient will not feel the needle enter their skin. With the continued depression of the rounded top 32 the fluid 35a, that is preferably an anesthetic chemical such as lidocaine, will flow therefrom through tube 35 and through the needle 36 to pass out of bevel 37 into the skin epidermis and to the nerve endings 28, as illustrated in FIG. 2. The nerve endings 28 are thereby deadened, as set out above, to allow a conventional shot to be administered in that deadened area.

The system 30 is preferably to be manufactured as a disposable item where the device is maintained in a sterile environment after manufacture and receives a liquid chemical, such as lidocaine, sealed therein for use in a single procedure only. Whereafter, the system 30 is disposed of. Additional systems 40 and 50, as shown in FIGS. 5 and 6, respectively, like system 30, are also intended to be manufactured as disposable items. Accordingly, both systems 40 and 50 preferably include bodies that each include a cup like end having a smooth uniform edge formed around an open interior and are arranged to receive a force applied through the cup for urging that cup end edge into the stratum corneum surface of a patient's epidermis layer of skin. As described above, the skin is thereby formed into a bubble or dome within the cup and a bevel end of a small needle is passed into that bubble or dome area. A local anesthetic is dispensed through the small needle bevel into the bubble or dome of skin, just below the skin surface, that flows into, so as to deaden the nerve endings. A shot utilizing a conventional hypodermic needle can then be administered through that deadened area.

System 40 to provide the above set out arrangement, as shown in FIG. 5, includes a housing 41 that is shaped like the bottom section of the housing of the system 30. Housing 41 includes a large diameter mid-section that slopes inwardly into a round bottom neck 42 that is open thereacross. The system 40 is operated essentially as described above with respect to a discussion of the operation of system 30. Except that, an inwardly extending lip 43 is provided around the body 41 midsection that an operator presses against. The operator applies such pressure with their fingers to urge the round bottom neck 42 edge into the patient's skin, forming a dome of skin within the round bottom neck 42. Thereafter, a bulb 44, that is shown as formed in the shape of a clown head, as an example of an aesthetically pleasing shape that is appropriate for use with system 40, is squeezed. Squeezing bulb 44 pressurizes a fluid contained within a tube that is arranged within the body 41. The tube, in turn, connects to, to pass that fluid through, a needle and out of the needle end 45 that extends just below the bottom neck 42, functioning as described above with respect to the discussion of system 30. Which fluid containing tube and needle are not shown in FIG. 5 but should be taken as being like the arrangement of system 30 shown in FIG. 4. Like the operation of system 30, as shown in FIGS. 3 and 4 and as described above, forming of a dome of skin within the round bottom neck 42 of the system 40, along with a slight movement of the neck into the dome, as may be needed to cause the needle end 45 to penetrate sufficiently into the skin epidermis layer, above the nerve endings to pass an anesthetic fluid therein to flow into the skin. Thereafter, by squeezing of bulb 44, an anesthetic fluid is injected into, so as to flow within, the patients skin. This flow deadens the area around the needle puncture, including the nerve endings, to then receive an injection of a medicine administered thereat, as with a conventional hypodermic needle.

FIG. 6 shows system 50 as a fourth embodiment to include a short flat cylindrical end section 52 wherefrom an arm 53 extends outwardly at essentially a right angle from the side thereof. The arm 53, as shown, terminates in a cup 54 end that includes a flat bottom edge 55 and is open across the cup interior. Like systems 30 and 40, system 50 includes a fluid containing tube, not shown, connected to be pressurized to urge fluid from the tube through a needle mounted to a tube end. As with operation of systems 30 and 40, as described above, depression of the cup 54 by application of a force to the top thereof, urges the cup edge 55 into a patient's skin forming a dome of skin within the cup. As that dome is formed a needle end 56 enters the patient's skin within the cup and with a slight movement of the cup into the skin, as may be needed, the needle end passes into the skin, above the nerve endings. Whereafter, to pass an anesthetic chemical through needle end 56, opposing parallel faces 52a and 52b of a body 51 are shown arranged as opposing surfaces of a bulb or bellows as the pressurizing arrangement, are pressed towards one another, generating a flow of air under pressure which pressurized flow travels into the fluid containing tube and out through the needle end 56, as described above with respect to the discussion of systems 30 and 40.

Hereinabove has been set out preferred embodiments of our invention in local anesthetic injection systems as are shown and described herein for injecting a local anesthetic, such as lidocaine, into an area of a patient's skin to deaden that area to pain to receive an injection from a conventional hypodermic needle therethrough and is particularly well suited for use with small children. It should, however, be understood that the present disclosure is made by way of example only and that variations and changes to the embodiments of the invention as shown and described are possible without departing from the subject matter coming within the scope of the following claims, and a reasonable equivalency thereof, which claims we regard as our invention.

THE CLAIMS

We claim:

1. A local anesthetic injection system comprising, a cup that is a short cylinder having an upstanding wall with a flat lower edge formed around an open area and includes a top surface formed at a right angle across a top edge of said upstanding wall whereagainst an operator can exert a force to press said flat edge onto a patient's skin surface to cause said skin within said cup to form into a dome shape; a hollow needle having a lower bevel end maintained within said cup such that said needle bevel end will pass beneath the skin surface formed into said dome shape, above nerve ends; a tube having a forward and rear end for containing said hollow needle, said tube is secured at a forward end into said upstanding wall and is connected at said rear end to a nozzle end of a hypodermic cylinder and said hypodermic cylinder contains a plunger as a means for passing a local anesthetic through said hollow needle and out of said needle bevel end into said skin that has been formed into said dome shape.

2. A local anesthetic injection system as recited in claim 1, wherein the tube is a straight open sleeve that has its rear end arranged for releasable connection to the hypodermic nozzle end of the hypodermic cylinder, and said sleeve rear end is formed to slide onto and to bind onto said hypodermic nozzle end.

3. A local anesthetic injection system as recited in claim 1 wherein the hollow needle is maintained in the cup such that the needle bevel end will extend to just below the cup flat edge and is essentially parallel to the surface of the section of skin contained within said cup.

\* \* \* \* \*